(12) United States Patent
Borenstein et al.

(10) Patent No.: US 9,597,441 B2
(45) Date of Patent: Mar. 21, 2017

(54) MICROFLUIDIC ORGAN ASSIST DEVICE INCORPORATING BOUNDARY LAYER DISRUPTERS

(71) Applicant: Johnson & Johnson Innovation LLC, New Brunswick, NJ (US)

(72) Inventors: Jeffrey T. Borenstein, Newton, MA (US); Joseph L. Charest, Cambridge, MA (US); Chris DiBiasio, Stoughton, MA (US); Violet Finley, Medford, MA (US)

(73) Assignee: Johnson & Johnson Innovation LLC, New Brunswick, NJ (US)

(*) Notice: Subject to any disclaimer, the term of this patent is extended or adjusted under 35 U.S.C. 154(b) by 0 days.

(21) Appl. No.: 14/487,915

(22) Filed: Sep. 16, 2014

(65) Prior Publication Data

US 2015/0076067 A1  Mar. 19, 2015

Related U.S. Application Data

(60) Provisional application No. 61/878,394, filed on Sep. 16, 2013.

(51) Int. Cl.
*A61M 1/16* (2006.01)
*B01D 61/08* (2006.01)
*B01D 63/08* (2006.01)
*B01D 61/28* (2006.01)

(52) U.S. Cl.
CPC .......... *A61M 1/1621* (2014.02); *B01D 61/28* (2013.01); *B01D 63/082* (2013.01); *B01D 63/085* (2013.01); *B01D 63/088* (2013.01); *B01D 2313/14* (2013.01); *B01D 2325/08* (2013.01)

(58) Field of Classification Search
CPC .................................................. B01D 2325/06
See application file for complete search history.

(56) References Cited

U.S. PATENT DOCUMENTS

| | | | |
|---|---|---|---|
| 4,383,921 A * | 5/1983 | Bellhouse et al. | 210/321.72 |
| 5,254,259 A * | 10/1993 | Bellhouse et al. | 210/650 |
| 7,955,504 B1 | 6/2011 | Jovanovic et al. | |
| 2004/0256233 A1 | 12/2004 | Yonish | |
| 2005/0116161 A1 | 6/2005 | Hafeman et al. | |
| 2007/0017633 A1 * | 1/2007 | Tonkovich et al. | 156/300 |
| 2007/0059763 A1 | 3/2007 | Okano et al. | |

(Continued)

OTHER PUBLICATIONS

PCT/US14/55906: International Search Report and Written Opinion mailed Dec. 4, 2014.

*Primary Examiner* — Krishnan S Menon
*Assistant Examiner* — Bradley R Spies
(74) *Attorney, Agent, or Firm* — Venable LLP/Johnson & Johnson

(57) ABSTRACT

The general disclosure discusses a system and method for improving the efficacy of blood filtration treatments such as hemodialysis, hemofiltration, and hemodiafiltration. More particularly, the disclosure discusses a microfluidic device that includes first and second channels separated by a permeable membrane. One of the channels is configured for blood flow and includes a protein gel disruption layer. The protein gel disruption layer includes a plurality of elements at least partially extending across the blood flow channel that reduce the formation of a boundary layer or gel layer at the blood-membrane interface.

15 Claims, 13 Drawing Sheets

(56) References Cited

U.S. PATENT DOCUMENTS

| | | |
|---|---|---|
| 2010/0326914 A1 | 12/2010 | Drost et al. |
| 2011/0152107 A1 | 6/2011 | McGrath et al. |
| 2011/0158847 A1* | 6/2011 | Charest et al. ............... 422/45 |
| 2011/0312673 A1 | 12/2011 | Silverbrook et al. |
| 2012/0058302 A1* | 3/2012 | Eggenspieler et al. ....... 428/141 |
| 2012/0322097 A1 | 12/2012 | Charest et al. |
| 2013/0144266 A1 | 6/2013 | Borenstein et al. |
| 2014/0190884 A1 | 7/2014 | DiBiasio et al. |
| 2014/0197101 A1 | 7/2014 | Harjes et al. |

* cited by examiner

MICROFLUIDIC ORGAN ASSIST DEVICE INCORPORATING BOUNDARY LAYER DISRUPTERS

CROSS-REFERENCE TO RELATED PATENT APPLICATIONS

This application claims priority to U.S. Provisional Patent Application 61/878,394, filed on Sep. 16, 2013 and titled "SYSTEM AND METHOD FOR DISRUPTING BOUNDARY LAYERS IN MICROFLUIDIC DEVICES," which is incorporated herein by reference in its entirety.

BACKGROUND OF THE DISCLOSURE

Previous methods of achieving higher dialysis efficiencies, such as extending treatment time or flow rates, are inconvenient and expensive and can result in additional complications and problems with patient safety and quality of life. These methods can also result in undesirable effects on the blood.

SUMMARY OF THE DISCLOSURE

According to one aspect of the disclosure, a microfluidic device includes a first layer defining a first channel therein. The microfluidic device also includes a second layer defining a second channel therein. The second channel overlaps the first channel along a substantial portion of the length of the first channel. A membrane separates the first channel from the second channel. The device also includes a protein gel disruption layer adjacent to or positioned within the first channel or adjacent to the first channel. The protein gel disruption layer includes a plurality of elements at least partially extending across the first channel. The elements have a height of at least about 1 μm and have an end terminating at a distance from the center of the thickness of the membrane that is less than or equal to about ⅓ of a height of the first channel.

In some implementations, the microfluidic device also includes a third layer defining a third channel therein. The third channel overlaps the first channel. The microfluidic device can also include a second membrane separating the third channel from the first channel.

In some implementations, the plurality of elements extend fully across the first channel.

In some implementations, a height of the first channel is between about 50 μm and about 100 μm. In some implementations, the elements of the gel disruption layer include a plurality of topographical features integrated into the membrane. In some implementations, the gel disruption layer includes a screen disposed in the first channel and adjacent to the membrane. The screen defines a plurality of screen openings. A dimension of each of the plurality of screen openings along the length of the channel is between about 100 μm and about 5 mm. The screen includes one of a biocompatible metal, polyester, and a polyamide. A pitch between each of the plurality of elements is between about 100 μm and about 5 mm.

In some implementations, the length of the first channel is between about 5 cm and about 30 cm. In some implementations, the height of each of the plurality of elements is between about 1 μm and about 3 μm. In certain implementations, the first channel is configured for blood flow and the second channel is configured for infusate, dialysate, or oxygen flow. A height of each of the plurality of elements is equal to about a height of a gel layer in some implementations. In some implementations, each of the plurality of elements extends fully across the first channel.

Each of the plurality of elements extends from a surface opposite the membrane toward the membrane. In some implementations, each of the plurality of elements is integral to the first polymer layer and extends across the first channel adjacent to the membrane.

According to another aspect of the disclosure, a method includes providing a microfluidic device. The microfluidic device includes a first layer that defines a first channel therein. The microfluidic device also includes a second layer defining a second channel therein. The second channel overlaps the first channel along a substantial portion of the length of the first channel. The microfluidic device further includes a membrane separating the first channel from the second channel. The microfluidic device also includes a protein gel disruption layer adjacent to or positioned within the first channel. The protein gel disruption layer includes a plurality of elements extending at least partially across the first channel. The elements have a height of at least about 1 μm and an end terminating at a distance from the center of the thickness of the membrane that is less than or equal to about ⅓ of a height of the first channel. The method also includes flowing blood through the first channel, and a treatment fluid through the second channel.

In some implementations, the method also includes flowing the blood over the plurality of elements to generate disturbances in the laminar flow of the blood through the first channel. In some implementations, the treatment fluid includes dialysate and the method can also include transferring a waste material from the blood to the dialysate.

In some implementations, the treatment fluid includes oxygen and the method includes transferring oxygen from the second channel to blood flowing through the first channel. In some implementations, a pitch between each of the plurality of elements is between about 100 μm and about 5 mm. The height of the first channel is between about 50 μm and about 100 μm. In some implementations, each of the plurality of elements extends from a floor of the first channel toward the membrane. In some implementations, the height of each of the plurality of elements is between about 1 μm and about 3 μm.

According to another aspect of the disclosure, a method includes providing a microfluidic device. The microfluidic device includes a first layer defining one or more blood flow channels. The microfluidic device also includes a second layer defining one or more treatment fluid flow channels. The one or more treatment fluid flow channels overlap the one or more blood flow channels along a substantial portion of the length of the one or more blood flow channels. A membrane separates the one or more blood flow channels from the one or more treatment fluid flow channels. The microfluidic flow device includes a protein gel disruption layer adjacent to or positioned within the one or more blood flow channels. The protein gel disruption layer includes a plurality of elements extending at least partially across the one or more blood flow channels. The method also includes flowing blood through the one or more blood flow channels and flowing a treatment fluid through the one or more treatment fluid flow channels. Flowing the blood over the plurality of elements generates disturbances in the laminar flow of the blood through the one or more blood flow channels.

In some implementations, the treatment fluid includes one of dialysate and oxygen.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1A:
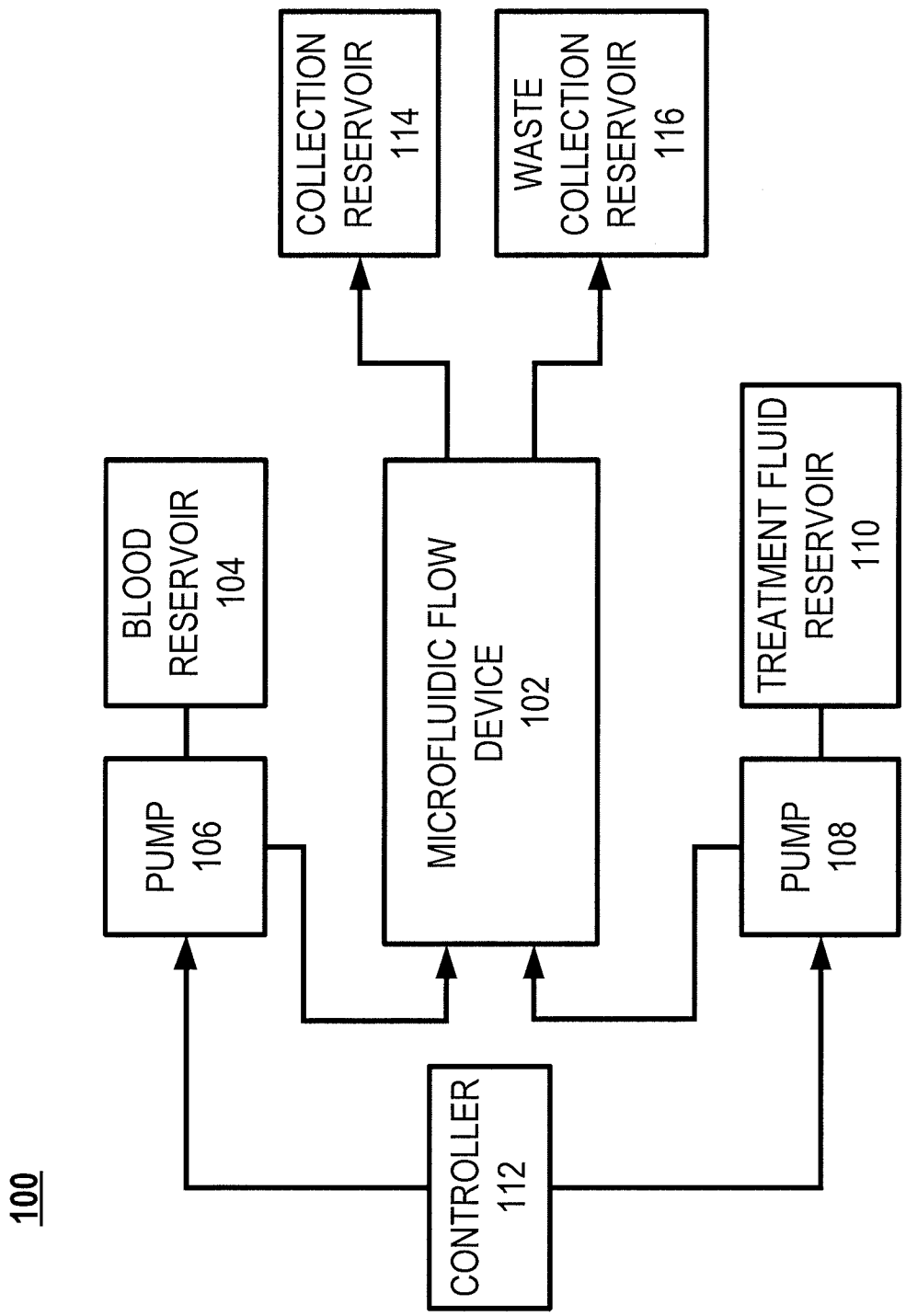
FIG. 1A illustrates a block diagram of an example system for use with a microfluidic flow device with a protein gel disruption layer.

FIG. 1A illustrates a block diagram of an example system 100 for use with a microfluidic flow device 102. Blood from a blood reservoir 104 is pumped through one or more blood flow channels of the microfluidic flow device 102 by a first pump 106. A second pump 108 pumps treatment fluid (e.g., oxygen, dialysate, or infusate) from a treatment fluid reservoir 110 through one or more treatment fluid channels of the microfluidic flow device 102. The first pump 106 and the second pump 108 are controlled by a controller 112. Blood exiting the microfluidic flow device 102 is collected in a collection reservoir 114 and spent treatment fluid or other waste exiting the microfluidic flow device 102 is collected in the waste collection reservoir 116. In some implementations, a plurality of treatment fluids is flowed through the microfluidic flow device 102. For example, and as described further in relation to FIG. 6, an infusate can be flowed through the microfluidic flow device 102 when the microfluidic flow device 102 is configured for convective clearance. The infusate passes into the blood to maintain fluid pressure as waste passes into dialysate flowing through the microfluidic flow device 102.

The system 100 includes a controller 112 that controls the first pump 106 and the second pump 108. In some implementations, the controller 112 includes one or more physical or graphical user interface knobs, controls, or switches that enable a user to control the flow rate of fluids through the microfluidic flow device 102. In some implementations, the controller 112 is a general purpose computing device. For example, the controller 112 can be a laptop, tablet computer, or smartphone. In other implementations, the controller 112 is a special purpose computer device. The controller 112 includes one or more processors and at least one computer readable medium, such as a hard drive, compact discs, or other storage device. Processor executable instructions are stored on the computer readable medium. When executed, the instructions cause the controller 112 to perform the functions and methods described herein. For example, the controller 112 controls the first pump 106 and the second pump 108 to flow blood and dialysate (or other fluid), respectfully, through the microfluidic flow device 102. In some implementations, the controller 112 controls the first pump 106 and the second pump 108 to have different flow rates.

The system 100 also includes the first pump 106 and the second pump 108 for flowing fluid through the microfluidic flow device 102. The first pump 106 and the second pump 108 are configured to generate a substantially laminar flow of fluid through the channels of the microfluidic flow device. In some implementations, a user controls the fluid flow rate of the fluid through the microfluidic flow device 102 with the above described controller 112. In some implementations, the first pump 106 and the second pump 108 are syringe pumps, peristaltic pumps, any other medical grade pump.

As illustrated, the system 100 also includes the blood reservoir 104, the treatment fluid reservoir 110, the collection reservoir 114, and the waste collection reservoir 116 (collectively referred to as reservoirs) for storing fresh and waste materials. In some implementations, one or more of the reservoirs include heating and mixing elements. For example, the blood reservoir 104 may include a heating element to heat the blood to near body temperature and the collection reservoir 114 may also include a mixer or agitator to help reduce the likelihood of clots forming in the blood stored in the collection reservoir 114. In some implementations, the first pump 106 is coupled directly to a vein of a patient rather than the blood reservoir 104, and the blood exiting the microfluidic flow device 102 is returned directly to the patient rather than to the collection reservoir 114.

Figure 1B:
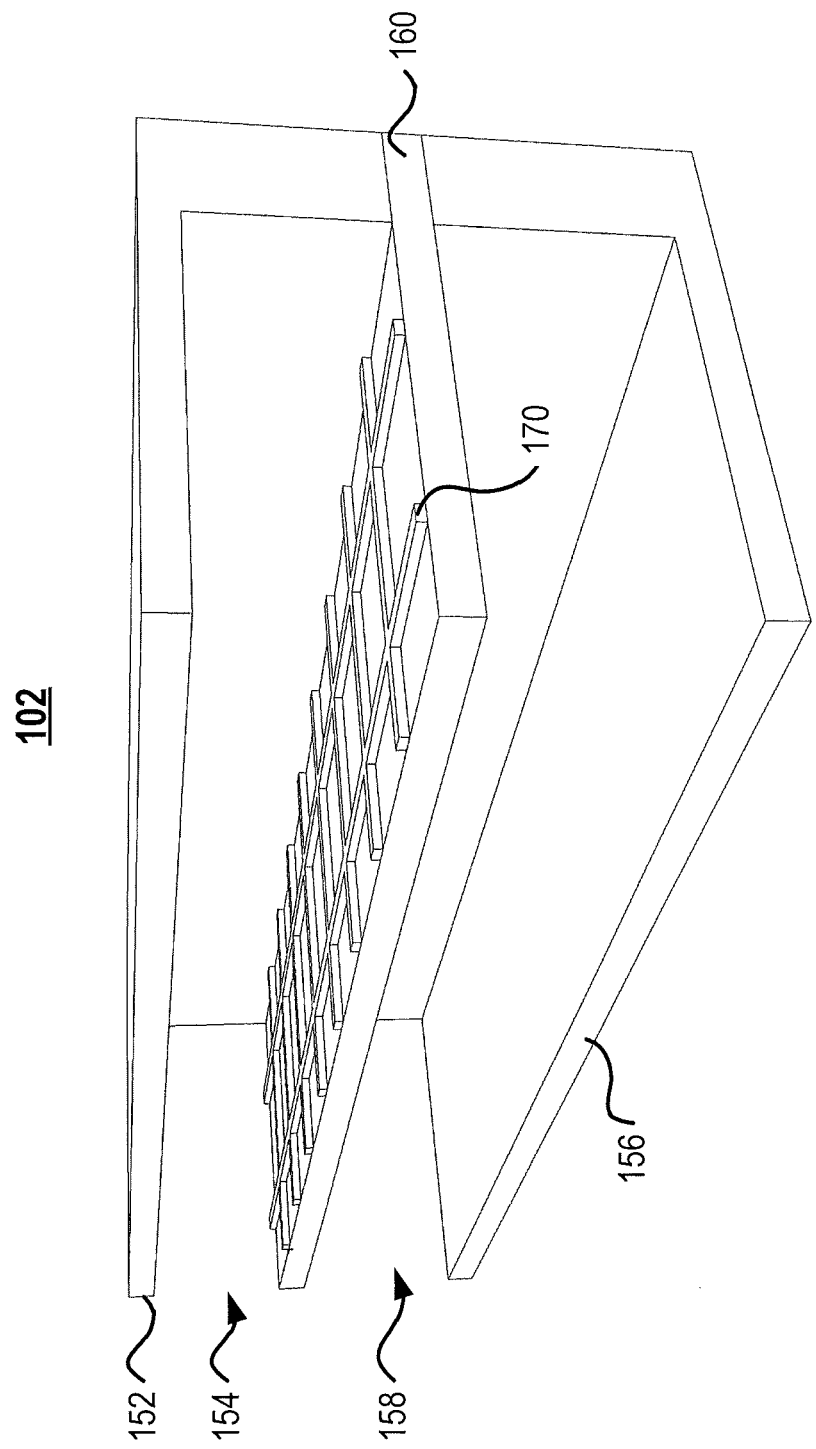
FIG. 1B illustrates a cut-away, perspective view of the microfluidic flow device from the system illustrated in FIG. 1A.

The system 100 also includes a microfluidic flow device 102. FIG. 1B illustrates a cut-away, perspective view of the microfluidic flow device 102. As illustrated in FIG. 1B, one wall of the microfluidic flow device 102 has been removed to illustrate the interior length of the microfluidic flow device 102. Different configurations of the microfluidic flow device 102 are described in further detail below in relation to FIGS. 2-6, but briefly, the microfluidic flow device 102 includes a first channel 154 configured for blood flow. The first channel 154 is defined in a first polymer layer 152. The microfluidic flow device 102 also includes a second channel 158 defined in a second polymer layer 156. The second channel 158 is configured for the flow of a treatment fluid, such as dialysate, infusate, oxygen, or combination thereof. A membrane 160 separates the first channel from the second channel. The membrane 160 enables fluidic communication between the blood flowing through the first channel 154 and the treatment fluid flowing through the second channel 158. In some implementations, the first channel 154 and the second channel 158 have a height in the range of about 10 µm to about 1 mm, about 10 µm to about 500 µm, about 10 µm to about 250 µm, or about 50 µm to about 100 µm and a width in the range of about 50 µm to about 1.5 millimeters. In some implementations, the width of each channel is less than about 900 µm. In some implementations, a single second channel 158 can span a plurality of first channels 154. For example, a single second channel 158 in the second polymer layer 156 may span five first channels 154 in the first polymer layer 152. In some implementations, the first channel 154 and second channel 158 may include one or more ribs or posts that support the membrane 160 and prevent the membrane 160 from deflecting into one of the first channel 154 or the second channel 158.

The first channel 154 includes a protein gel disruption layer 170. As illustrated, the protein gel disruption layer 170 is a screen disposed over the membrane 160. The protein gel disruption layer 170 in the first channel includes a plurality of elements that extend across the first channel and frustrate or prevent the formation of a boundary layer or gel layer at the blood-membrane interface. As described below, the protein gel disruption layer 170 can include a screen, film, mesh, strut, joist, or combination thereof.

In some implementations, the protein gel disruption layer can improve the efficacy and performance of the mass transfer through the membrane of the microfluidic flow device 102 by substantially keeping the membrane free of blood proteins (or other boundary layers and solutes) that can build up over time during use of the microfluidic flow device 102. The proteins and solutes can coagulate at the membrane surface and prevent materials from passing through the one or more membranes. In some implementations, the elements of the protein gel disruption layer cause minor disturbances in the laminar flow of the blood through the one or blood flow channels. In some implementations, the disturbances in the laminar flow of the blood occur substantially near the blood-membrane interface. For example, the flow disturbance is large enough to disrupt the formation of a gel or boundary layer at the blood-membrane interface, but not so significant as to cause deleterious flow-related effects on the blood. In some implementations, a height of the protein gel disruption layer is between about a height the gel layer would form if the microfluidic flow device 102 did not include the protein gel disruption layer and about ⅔ of the height of the blood flow channel. Estimating the height of the gel layer is discussed in relation to FIG. 7.

In some implementations, the channels of the microfluidic flow device 102 are defined in one or more polymer layers. Channels in different polymer layers are separated from one another at overlapping portions by a porous membrane. The layers of the microfluidic flow device 102 can be coupled together using a chemical adhesive, plasma bonding, by clamping the layers together, or a combination thereof. Each of the polymer layers can include a thermoplastic, such as polystyrene or polyimide, biodegradable polyesters, such as polycaprolactone (PCL), or soft elastomers such as polyglycerol sebacate (PGS). In other implementations, the polymer layers include polydimethylsiloxane (PDMS) or poly(N-isopropylacrylamide). In other implementations, each layer of the microfluidic flow device 102 includes non-polymer materials such as, but not limited to, ceramics; metals, glasses, nanotubes or nanowires formed from, for example, carbon or zinc oxide; or other nonpolymer materials. The channels defined by the layers are fabricated into each of the layers using, for example, photolithographic techniques, injection molding, direct micromachining, deep reactive ion etching, hot embossing, or any combinations thereof.

Figure 1C:
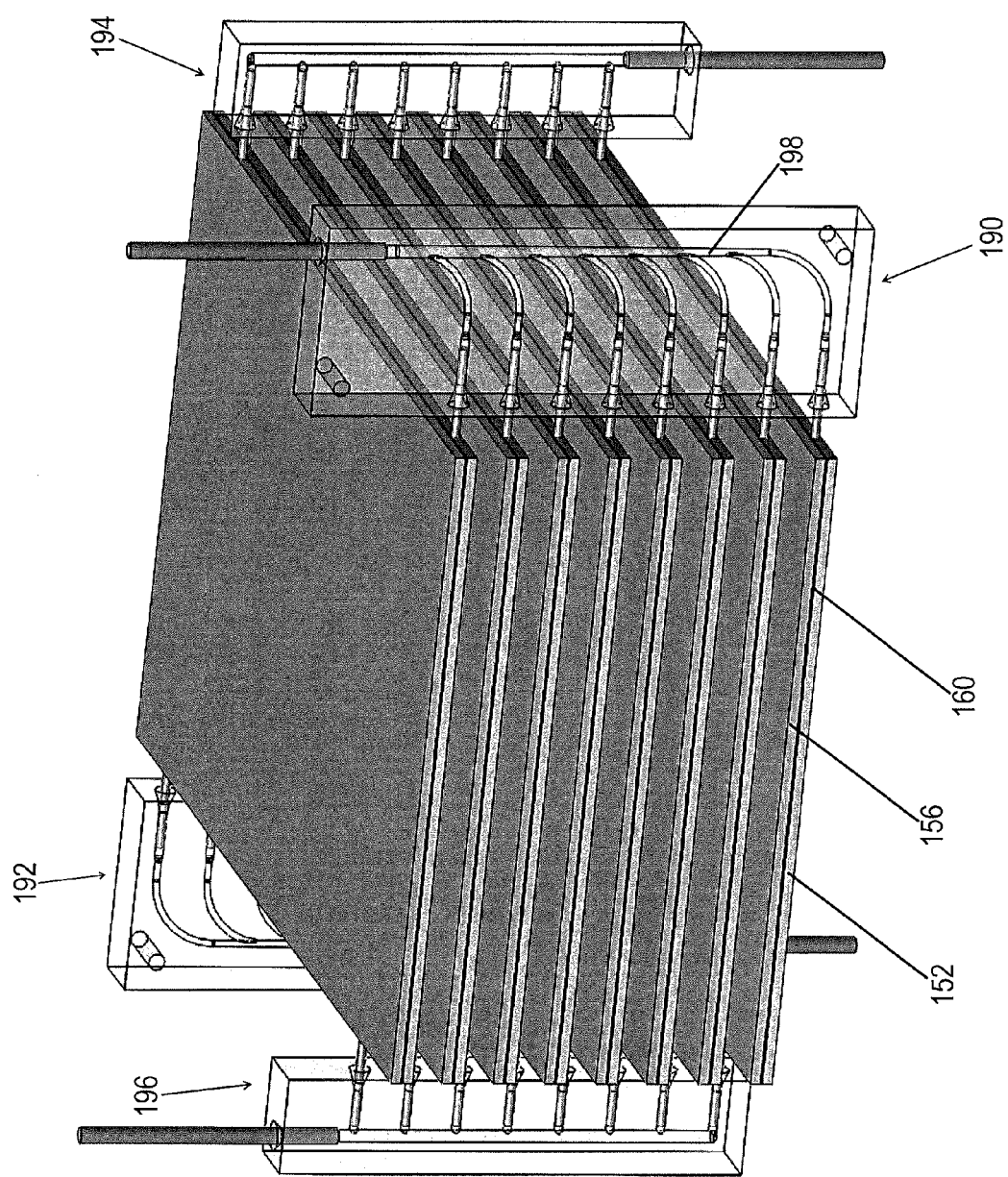
FIG. 1C illustrates another example microfluidic device composed of eight bilayers, the example microfluidic device is suitable for use in the system illustrated in FIG. 1A.

FIG. 1C illustrates an example microfluidic device 102 composed of eight bilayers that is suitable for use in the system 100. Each of the bilayers can be similar to the microfluidic device 102, illustrated in FIG. 1B. Each of the bilayers includes a first polymer layer 152 (also referred to as a blood substrate layer) and a second polymer layer 156 (also referred to as the treatment fluid substrate layer). As illustrated in FIG. 1B, each of the first polymer layers 152 is separated from its respective second polymer layer 156 by a membrane 160. Each of the first polymer layers 152 include a network of channels for blood flow and each of the second polymer layers 156 include a second network of channels for treatment fluid flow. A protein gel disruption layer can be positioned within or adjacent to each of the channels of the first polymer layers 152. The microfluidic device 102 also includes a blood inlet manifold 190 and a blood outlet manifold 192, both coupled to the first polymer layer. Similarly, a treatment fluid inlet manifold 194 and a treatment fluid outlet manifold 196 are coupled to the second polymer layer 156. Blood enters the channels of each of first polymer layer 152 through the blood inlet manifold 190 and exits through the blood outlet manifold 192. Treatment fluid enters the channels of each of the second polymer layers through the treatment fluid manifold 194 and exits through the treatment fluid manifold 196. In some implementations, first polymer layers 152 and the second polymer layers 156 each have a thickness in the range of about 10 µm to about 10 mm, and the membrane 160 has thickness in the range of about 500 nm to about 1 mm.

Figure 1D:
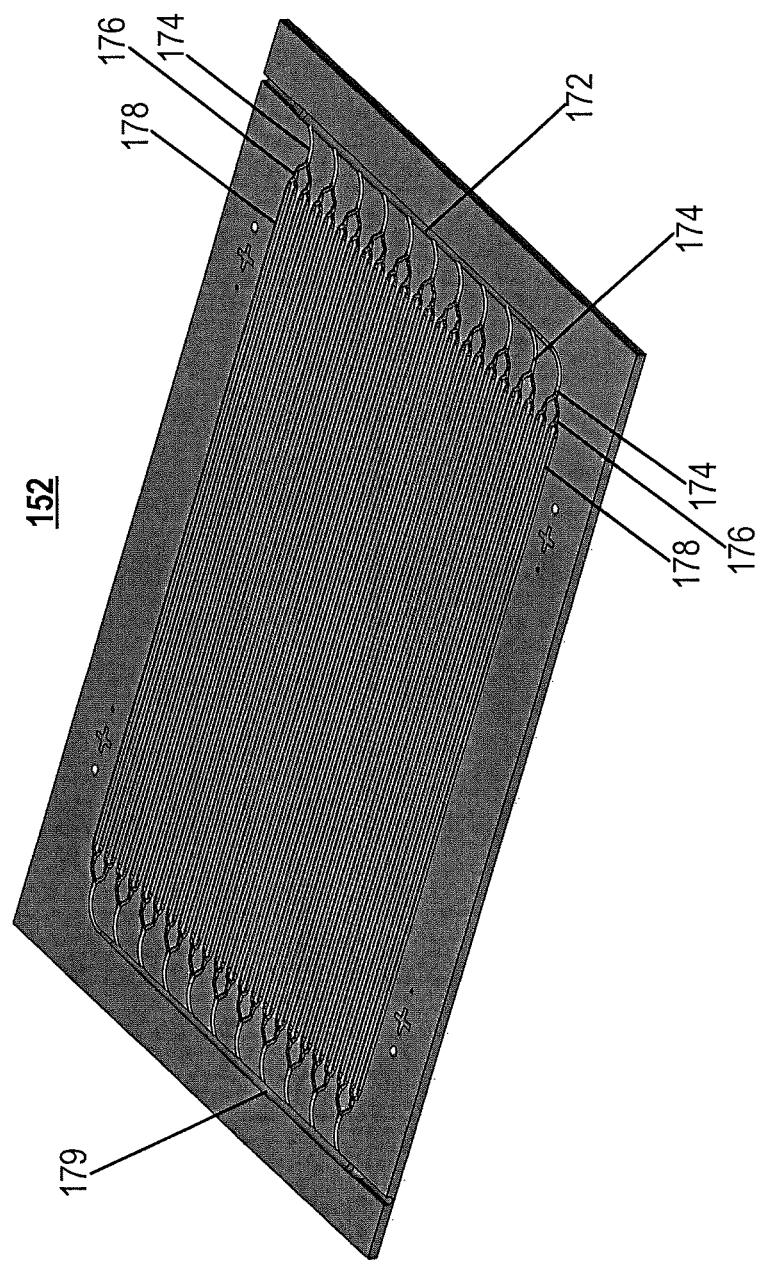
FIG. 1D illustrates a blood substrate layer suitable for use in the microfluidic device illustrated in FIG. 1C.

FIG. 1D illustrates a first polymer layer 152 suitable for use in the microfluidic device 102 of FIGS. 1A-1C. The first polymer layer 152 includes a network of channels, which includes a primary channel 172, secondary channels such as channel 174, tertiary channels such as channel 176, quaternary channels such as channel 178, and an outlet channel 179. In some implementations, a protein gel disruption layer can be positioned within or adjacent to each of, or a subset of, the channels—for example, the quaternary channels 178. The first polymer layer 152 has a thickness in the range of about 10 µm to 10 mm. In some implementations, each channel in the first polymer layer 152 (and second polymer layer 156) has a height in the range of about 10 µm to about 1 mm and a width in the range of about 50 µm to about 1.5 mm. In some implementations, the width of each channel is less than about 900 µm.

Figure 2:
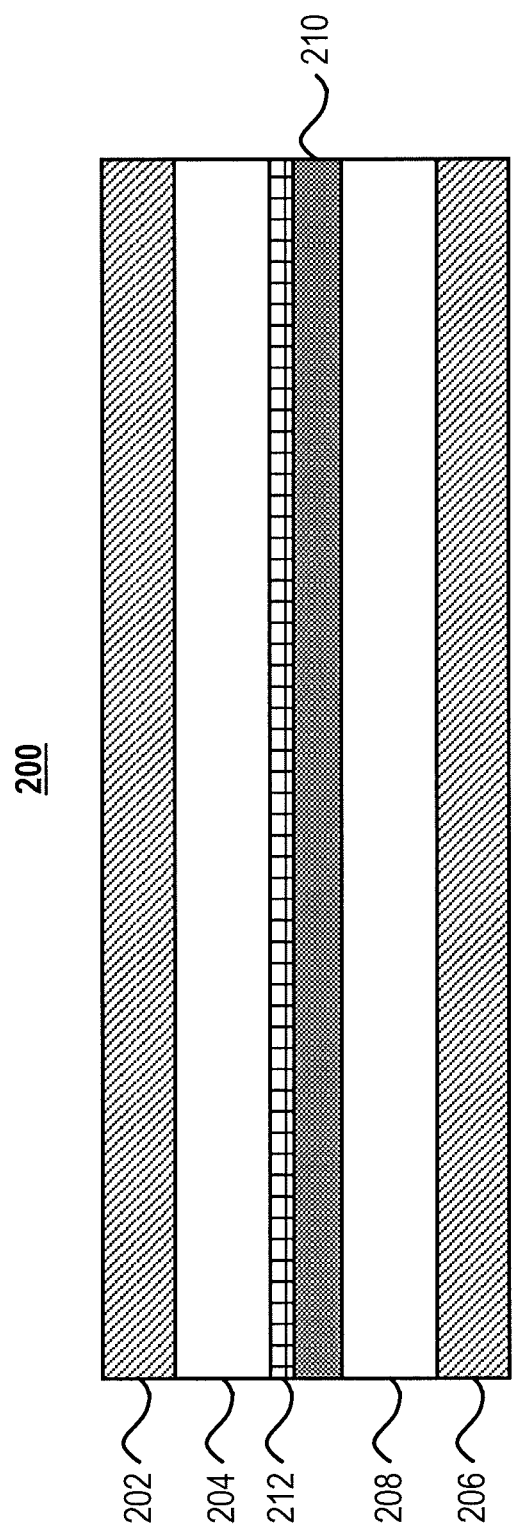
FIG. 2 illustrates a cross-sectional view of an example microfluidic flow device with an example screen protein gel disruption layer suitable for use in the system illustrated in FIG. 1A.

FIG. 2 shows a cross-section of an example microfluidic flow device 200 with an example protein gel disruption layer 212. The microfluidic flow device 200 includes a first polymer layer 202 defining a first flow channel 204. In some implementations, the first flow channel 204 is referred to as a blood flow channel. The microfluidic flow device 200 also includes a second polymer layer 206 that defines a second flow channel 208 (also referred to as a filtrate or oxygen channel). The first flow channel 204 and the second flow channel 208 overlap one another and are separated by a membrane 210. A protein gel disruption layer 212 is disposed within the first flow channel 204 and adjacent to the membrane 210. The protein gel disruption layer 212 is distributed along a substantial length (e.g., between about 60% to about 100%) of the first flow channel 204.

The example protein gel disruption layer 212 includes a screen disposed across the blood-facing surface of the membrane 210. In some implementations, the screen is formed from a plurality of fibers woven together. The weave of the fibers create a plurality of pores (or screen openings) in the protein gel disruption layer 212. In other implementations, the screen is formed by fusing a plurality of components together. For example, a plurality of horizontal rungs and a plurality of vertical rungs may be fused together to form a screen. In some implementations, each of the screen openings is at least one order of magnitude larger than the pores of the membrane 210. In some implementations, a dimension of each of the screen openings is defined by the pitch of the fibers within the weave of the screen. In some implementations, the pitch of the fibers parallel to the flow through the first flow channel 204 is the same as the pitch of the fibers horizontally transverse to the flow through the first flow channel 204—creating square screen openings. In other implementations, the pitch of the parallel fibers may be greater than or less than the pitch of the fibers transverse to the fluid flow. In other implementations, the screen can be configured such that the fibers of the screen run at an angle between about 15 degrees and about 75 degrees or between about 30 degrees and about 60 degrees with respect to a wall of the first flow channel. In some implementations, the pitch of the fibers is between about 100 µm and about 10 mm, between about 100 µm and about 5 mm, between about 100 µm and about 3 mm, between about 100 µm and about 1 mm, or between about 100 µm and about 500 µm. In some implementations, the height of the screen is between about 1 µm and about 5 µm, between about 1 µm and about 2.5 µm, or about the thickness of a gel protein layer that would form absent the protein gel disruption layer 212. In some implementations, the fibers of the screen include monofilament yarns manufactured from polyester (PET), polyamide (PA), other biocompatible fibers, or a combination thereof. In some implementations, the fibers of the screen are between about 1 µm and about 150 µm, between about 1 µm and about 100 µm, or between about 1 µm and about 50 µm.

In other implementations, the protein gel disruption layer 212 is a film disposed across the membrane 210. The film includes a plurality of pores to enable blood to interact with the membrane 210. Each of the pores of the film is at least an order of magnitude larger than the pores of the membrane 210. The film has a height between about 1 µm and about 5 µm, between about 1 µm and about 2.5 µm, or about the thickness of a gel protein layer that would form absent the protein gel disruption layer 212. In some implementations, each of the pores of the film is between about 100 µm and about 10 mm, between about 100 µm and about 5 mm, between about 100 µm and about 3 mm, between about 100 µm and about 1 mm, or between about 100 µm and about 500 µm wide. In some implementations, the space between each of the pores is between about 100 µm and about 10 mm, between about 100 µm and about 5 mm, between about 100 µm and about 3 mm, between about 100 µm and about 1 mm, or between about 100 µm and about 500 µm.

Figure 3:
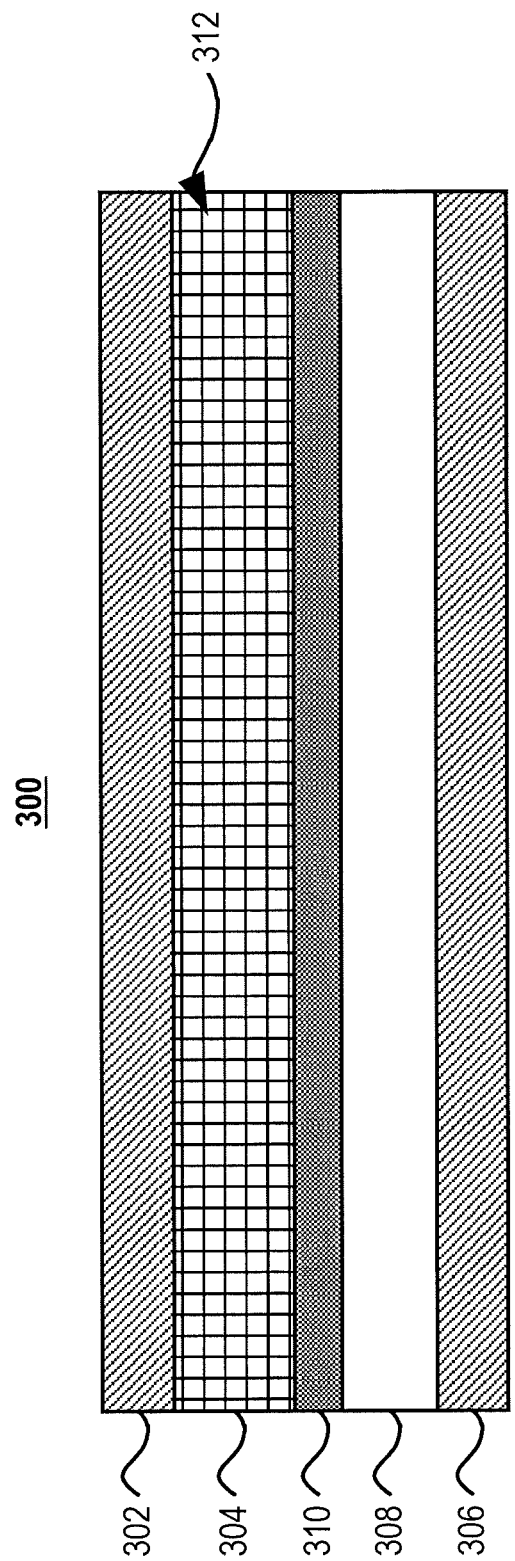
FIG. 3 illustrates a cross-sectional view of an example microfluidic flow device with another example mesh protein gel disruption layer suitable for use in the system illustrated in FIG. 1A.

FIG. 3 illustrates a cross-sectional view of an example microfluidic flow device 300 with another example protein gel disruption layer 312. The microfluidic flow device 300 includes a first polymer layer 302 defining a first flow channel 304 and a second polymer layer 306 defining a second flow channel 308. As illustrated in FIG. 3, the protein gel disruption layer 312 includes a mesh disposed in the first flow channel 304 (e.g., the blood flow channel). The protein gel disruption layer 312 spans substantial (e.g., about 60% to about 100%) portions of the length of the first flow channel 304 and is substantially the same height and width as the first flow channel 304. In some implementations, the protein gel disruption layer 312, in a mesh configuration, includes a plurality of fibers woven together to form a three-dimensional mesh. For example, the protein gel disruption layer 312 can include a plurality of fibers running parallel to the flow through the first flow channel 304, a plurality of fibers running horizontally transverse to the flow through the first flow channel 304, and a plurality of fibers running vertically perpendicular to the flow through the first flow channel 304. In some implementations, the pitch of the fibers in each of the three directions is between about 100 µm and about 10 mm, between about 100 µm and about 5 mm, between about 200 µm and about 4 mm, between about 300 µm and about 3 mm, between about 400 µm and about 2 mm, or between about 500 µm and about 1 mm. In other implementations, the protein gel disruption layer 312 includes non-woven meshes. The non-woven meshes can include sponges or sponge-like materials, porous foams, felt-like structures, cellulose, or a combination thereof.

Figure 4A:
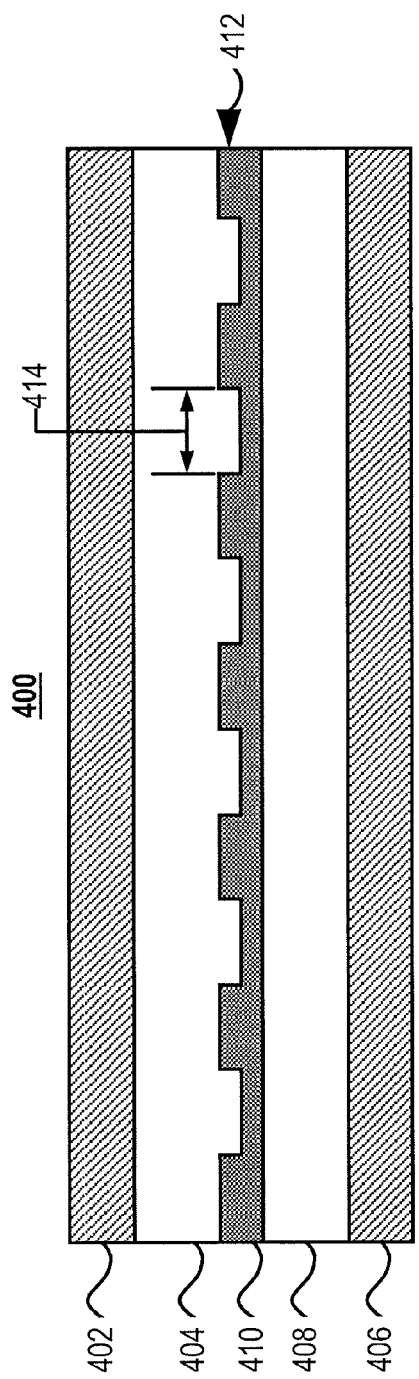
FIGS. 4A and 4B illustrate cross-sectional views of an example microfluidic flow device with another example protein gel disruption layer integrated into a membrane, the example microfluidic device is suitable for use in the system illustrated in FIG. 1A.

FIG. 4A illustrates a cross-sectional view of an example microfluidic flow device 400 with another example protein gel disruption layer 412. The microfluidic flow device 400 includes a first polymer layer 402 defining a first flow channel 404. The microfluidic flow device 400 also includes a second polymer layer 406 defining a second flow channel 408. The protein gel disruption layer 412 of the microfluidic flow device 400 is integrated into a membrane 410 separating the first flow channel 404 from the second flow channel 408. In some implementations, integrating the protein gel disruption layer 412 into the membrane 410 includes forming a topological pattern in the blood-facing surface of the membrane 410. The topographical pattern includes a plurality of elements 414 integrated into membrane 410. The elements 414 of the topographical pattern extend across the membrane 410 within the first flow channel 404. In some implementations, the topographical pattern of the protein gel disruption layer 412 is formed by track etching, milling, stamping, plating, hot embossing, or direct micromachining the membrane 410. In other implementations, protein gel disruption layer 412 is created by injection molding the membrane 410, where the mold includes the topographical pattern. In some implementations, the elements 414 of the protein gel disruption layer 412 include a plurality of grooves, pits, posts, ridges, or combination thereof formed into the membrane 410. In some implementations, the elements include a plurality of grooves or ridges that run transverse to the flow of fluid through the first flow channel 404. In other implementations, grooves and ridges run non-transverse to the flow of fluid through the first flow channel 404. For example, the grooves and ridges may be angled to between about 15 degrees and about 75 degrees or between about 30 degrees and about 60 degrees with respect to a wall of the first flow channel 404. In some implementations, the membrane 410 is between about 30 µm and about 125 µm thick. In some implementations, the depth of each of the features 414 (or the topographical pattern) of the protein gel disruption layer 412 is between about 1 µm and about 50 µm, between about 10 µm and about 40 µm, or about 20 µm and about 30 µm deep, or about the thickness of a gel protein layer that would form absent the protein gel disruption layer 412. In some implementations, the pitch between each of the features of the elements 414 is between about 100 µm and about 10 mm, between about 100 µm and about 5 mm, between about 100 µm and about 3 mm, between about 100 µm and about 1 mm, or between about 100 µm and about 500 µm.

Figure 4B:
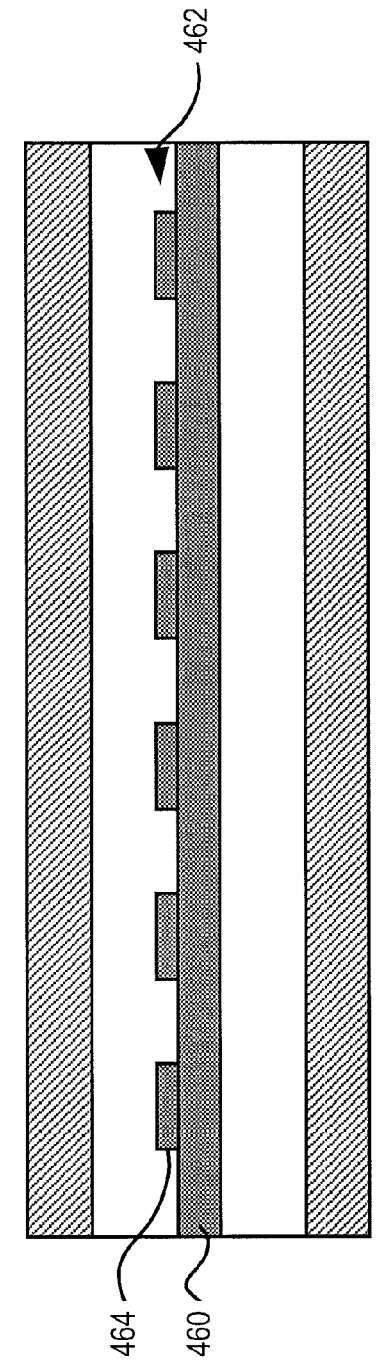

FIG. 4B illustrates a cross-sectional view of an example microfluidic flow device 450 with another example protein gel disruption layer 462. The protein gel disruption layer 462 includes a plurality of flow disruption features 464 disposed along a surface of the membrane 460. In some implementations, the flow disruption features 464 create a topographical pattern that extends across the 460 in the blood flow channel. In some implementations, each of the disruption features 464 is coupled to the membrane 460 with a chemical adhesive or with plasma bonding. In some implementations, the pitch between each of the features of the flow disruption features 464 is between about 100 µm and about 10 mm, between about 100 µm and about 5 mm, between about 100 µm and about 3 mm, between about 100 µm and about 1 mm, or between about 100 µm and about 500 µm.

In some implementations, the flow disruption features 464 are not affixed to the membrane 460. In these implementations, the flow disruption features 464 can form joists that are integral to or are embedded within the polymer layer and extend across an open portion of the first channel. In these implementations, the joists may physically contact the membrane 460 The joists may have a thickness (normal to the membrane 460) between about 1 µm and about 5 µm, between about 1 µm and about 2.5 µm, or about the thickness of a gel protein layer that would form absent the protein gel disruption layer 462 above the membrane 460.

Figure 4C:
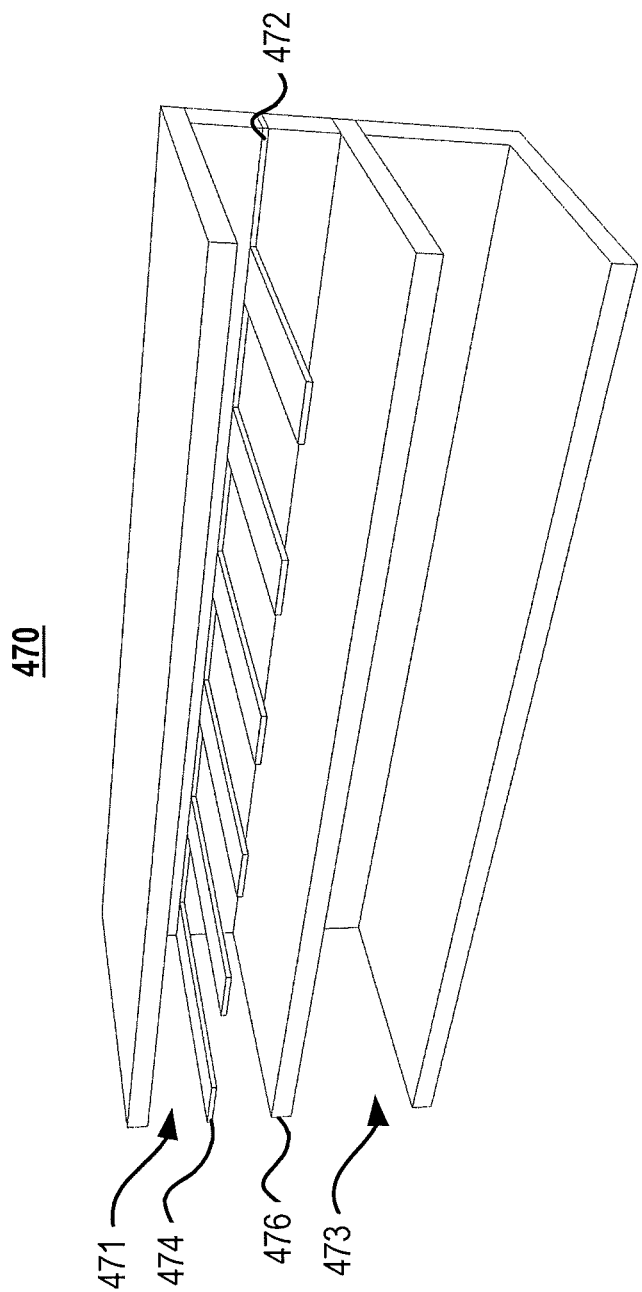
FIG. 4C illustrates cut-away, perspective view of an example microfluidic flow device with example center-strut protein gel disruption layer suitable for use in the system illustrated in FIG. 1A.

FIG. 4C illustrates cut-away, perspective view of an example microfluidic flow device 470 with an example mid-channel-strut protein gel disruption layer 472. The microfluidic flow device 470 is similar to the microfluidic flow device 102 shown in FIG. 1B. Like the microfluidic flow device 102, the microfluidic device 470 includes a first flow channel 471 separated from a second flow channel 473 by a membrane 476. The first channel 471 can be configured to serve as a blood flow channel and the second channel 473 can be configured to serve as a treatment fluid channel as described above.

In contrast to the microfluidic device 102 shown in FIG. 1B, the gel disruption layer 472 shown in FIG. 4C is positioned in the first channel 471 away from the membrane 476 as well as away from the floor of the first channel 471. The protein gel disruption layer 472 includes a plurality of flow disruption features 474 that span at least partially across a width of the first flow channel. Each of flow disruption features 474 extends out from a surface of the sidewall of the first flow channel. As illustrated in FIG. 4C, the flow disruption features 474 are disposed at about a center height of the first flow channel. In some implementations, the flow disruption features 474 may be disposed closer to or further from the membrane 476.

In some implementations, the distance between a terminating end (i.e., an end closest to the membrane 476 or floor of the first channel 471) of each of the flow disruption features 474 and the center of the thickness of the membrane 476 is less than or equal to about ⅓ of a height of the first flow channel. In some implementations, the flow disruption features 474 have a height between about ⅓ and about ⅔ of the height of the blood flow channel, and in other implementations, the flow disruption features 474 have a height between about 1 µm and about ⅓ of the height of the blood flow channel.

In some implementations, a surface of the flow disruption features 474 is configured to promote turbulence or disruptions in the laminar flow of blood through the blood flow channel. For example, the flow disruption features 474 may be rounded or have an airfoil-shaped to direct blood toward the membrane 476. In some implementations, the pitch between each of the features of the flow disruption features 474 is between about 100 µm and about 10 mm, between about 100 µm and about 5 mm, between about 100 µm and about 3 mm, between about 100 µm and about 1 mm, or between about 100 µm and about 500 µm.

In some implementations, each of the flow disruption features 474 includes a biocompatible metal or polymer (such as a polyester or a polyamide). In some implementations, each of the flow disruption features 474 are placed in the first flow channel by heating the flow disruption feature 474 and then pressing the heated flow disruption feature 474 into the walls of first flow channel, such that the flow disruption feature 474 spans the first flow channel. In other implementations, a filament is used to melt slots into either wall of the first flow channel to receive each of the flow disruption features 474. In some other implementations, the flow disruption features 474 are integral to the substrate or walls of the first flow channel. For example, the flow disruption feature 474 may be part of the mold used to form the first layer. In another example, the protein gel disruption layer 742 can include a plurality of larger struts running parallel to the flow through the first flow channel that form the sidewall of the flow channel, and a plurality of struts running horizontally transverse to the flow through the first flow channel that are fused together to position the strut at the proper height within the first flow channel.

Figure 5:
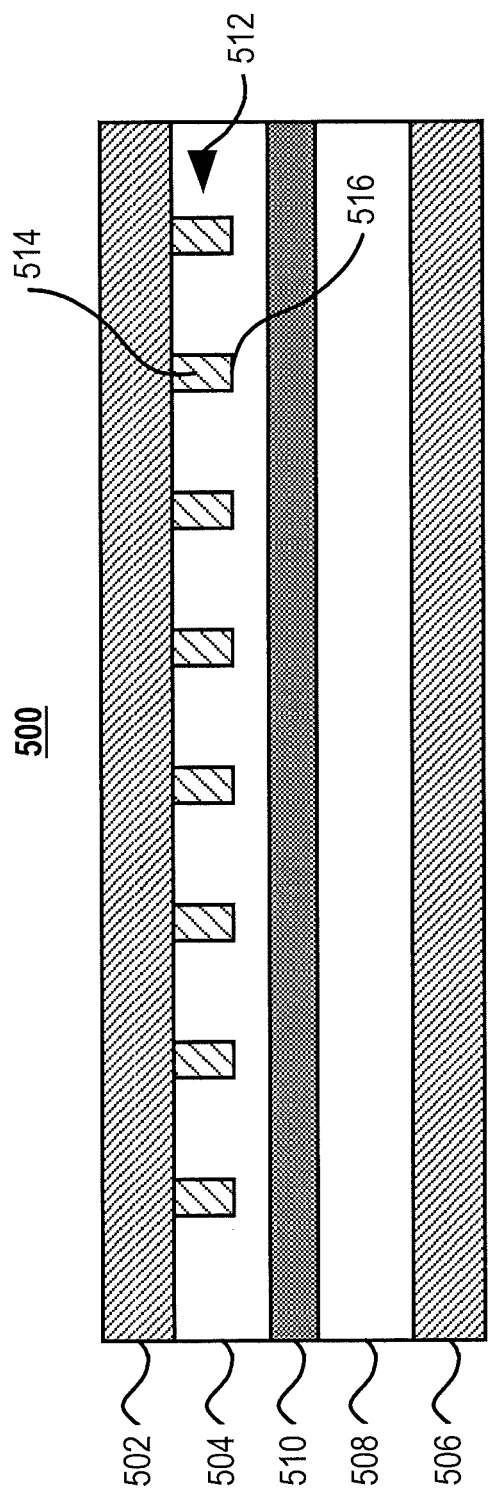
FIG. 5 illustrates a cross-sectional view of an example microfluidic flow device with another example strut protein gel disruption layer suitable for use in the system illustrated in FIG. 1A.

FIG. 5 illustrates an example microfluidic flow device 500 with another example protein gel disruption layer 512. The microfluidic flow device 500 includes a first polymer layer 502 defining a first flow channel 504, and a second polymer layer 506 defining a second flow channel 508. The protein gel disruption layer 512 includes a plurality of struts 514. Each of the plurality of struts 514 spans across a width of the first flow channel 504. In other implementations, one or more of the struts 514 do not span the entire width of the first flow channel 504. Each of the struts 514 extends from a surface of the first flow channel 504 (e.g., blood flow channel) opposite the membrane 510. The distance between the terminating end 516 of each of the struts 514 and the center of the thickness of the membrane 510 is less than or equal to about ⅓ of a height of the first flow channel 504. In some implementations, the pitch between each of the struts 514 is between about 100 µm and about 10 mm, between about 100 µm and about 5 mm, between about 100 µm and about 3 mm, between about 100 µm and about 1 mm, or between about 100 µm and about 500 µm.

In some implementations, each of the struts 514 includes a biocompatible metal, polyester, or a polyamide. In some implementations, each of the struts 514 are placed in the first flow channel 504 by heating the struts 514 and then pressing the heated strut 514 into the walls of first flow channel 504, such that the struts span the first flow channel 504. In other implementations, a filament is used to melt slots into either wall of the first flow channel 504 to receive each of the struts 514. In another implementation, the struts 514 are integral to the substrate. For example, the struts 514 may be part of the mold used to form the polymer layer.

Figure 6:
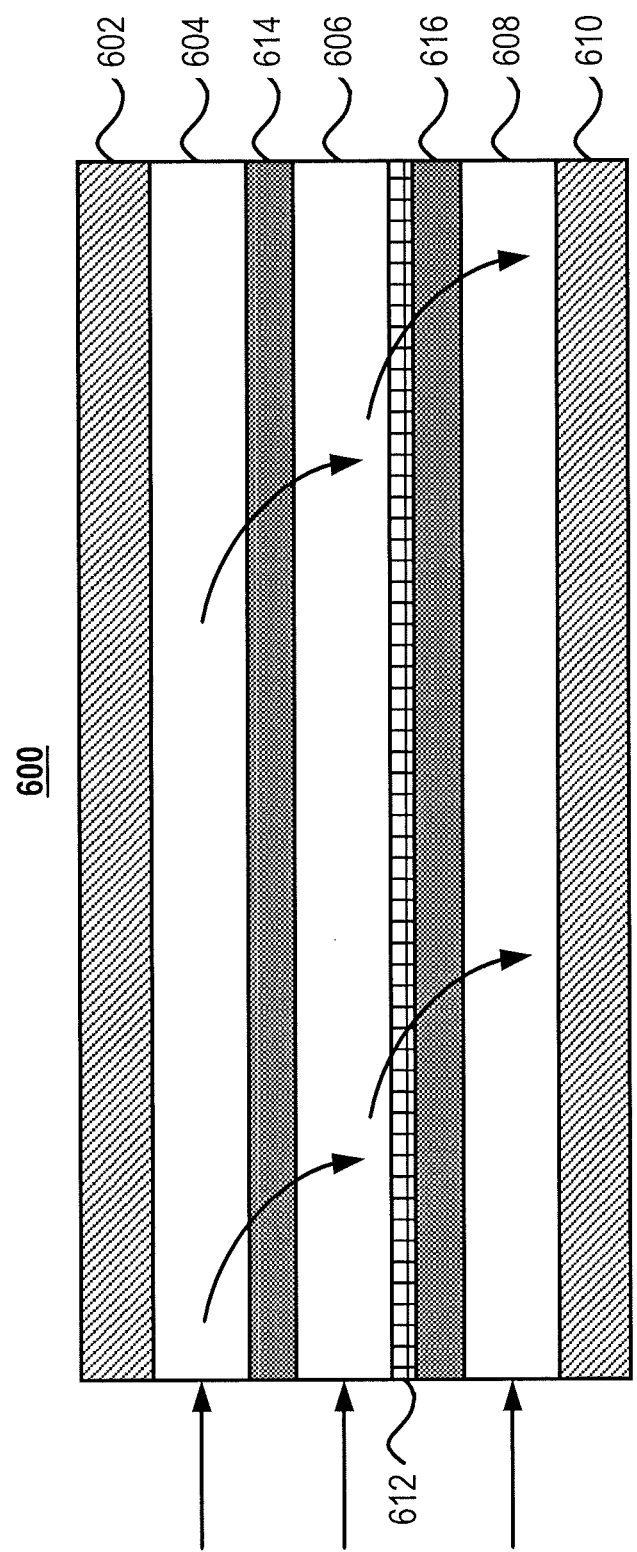
FIG. 6 illustrates a cross-sectional view of an example microfluidic device in a tri-layer configuration with a protein gel disruption layer suitable for use in the system illustrated in FIG. 1A.

FIG. 6 illustrates an example microfluidic device 600 with a protein gel disruption layer 612. The microfluidic device 600 is configured in a tri-layer configuration. In the tri-layer configuration, the microfluidic device 600 includes a first channel 604 defined in a first polymer layer 602, a second channel 606 defined in a second polymer layer, and a third channel 608 defined in a third polymer layer 610. The second channel 606 is separated from the first channel 604 and the third channel 608 at overlapping portions by membranes 614 and 616. The second channel 606 includes the protein gel disruption layer 612. As illustrated the protein gel disruption layer 612 is configured as a screen; however, any of the protein gel disruption layers described herein is acceptable for use in a tri-layer configuration. In some implementations, the tri-layer configuration operates using convective clearance. More particularly, blood is flowed through the second channel 606 and fresh infusate is flowed into the first channel at a predetermined rate and pressure. The transmembrane pressure gradient causes the infusate to pass through the first membrane 614 and into the blood in the second channel 606. Dialysate is flowed through the third channel 608. As the infusate flows from the first channel 604 and into the blood of the second channel 606, waste materials from the blood pass through the membrane 616 and into the third channel 608. The protein gel disruption layer 612 prevents the buildup of a protein gel layer or a boundary layer on the membrane 616, which can reduce the efficiency of the microfluidic device 600. In some implementations, the microfluidic device 600 can include a protein gel disruption layer 612 on each of the membranes in the microfluidic device 600.

Figure 7:
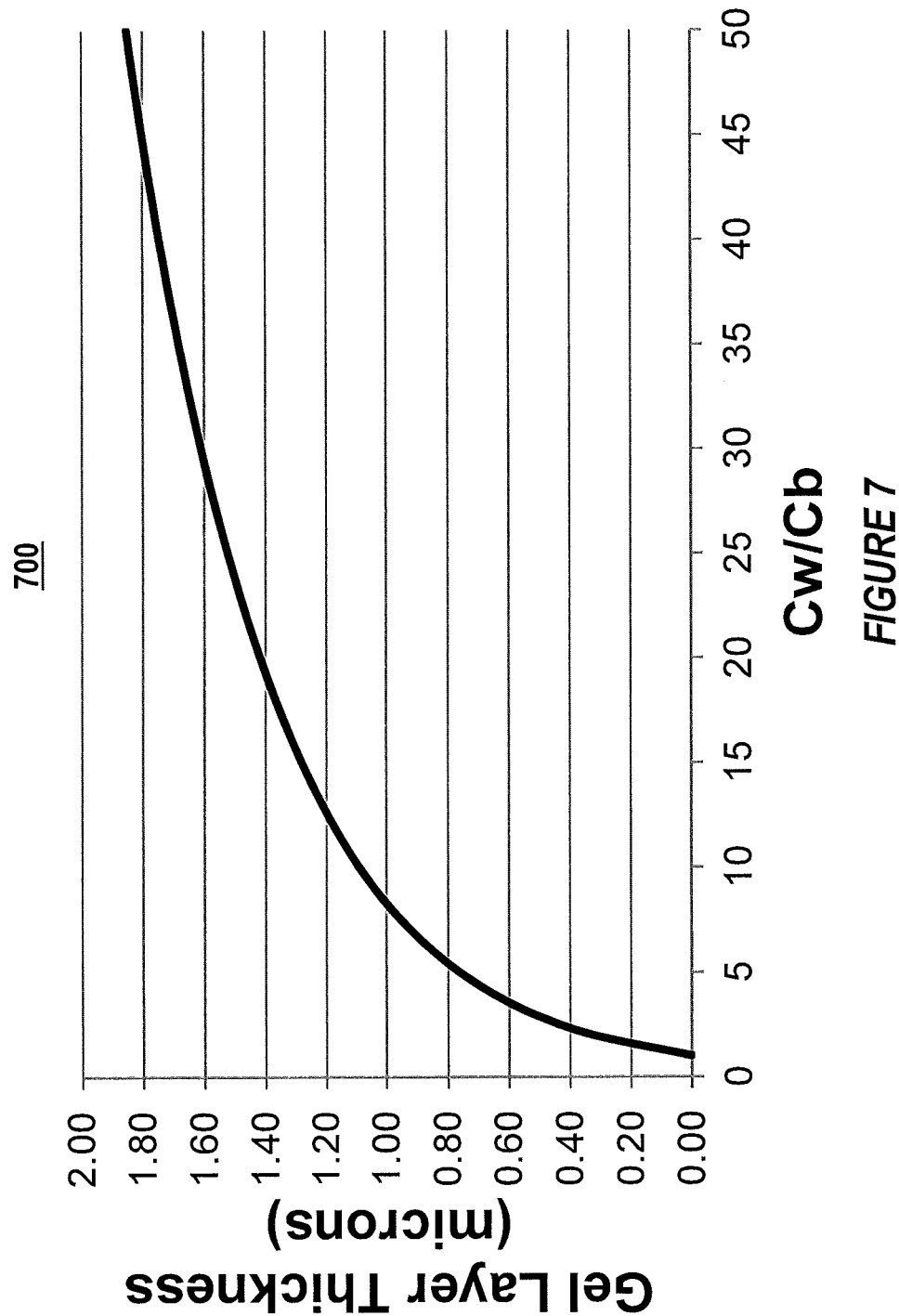
FIG. 7 illustrates an example graph of the protein gel layer thickness as a function of solute concentration ($C_w$) and blood plasma protein concentration ($C_b$).

FIG. 7 illustrates an example graph 700 of the protein gel layer thickness as a function of solute concentration ($C_w$) and blood plasma protein concentration ($C_b$). In some implementations, at steady state, the rate of solute transfer through a membrane can be calculated with Fick's first law. Under this assumption, the flux through the membrane is based on the solute concentration and the blood plasma protein concentration. The flux through the membrane can be calculated with the equation:

$$J_v dy = -D \frac{dC_w}{C_b} \quad (1)$$

In the above equation, $J_v$ is the flux through the membrane, $dy$ is the gel layer thickness, $D$ is the diffusion coefficient, and $dC_w/C_b$ is the concentration gradient between $C_w$ and $C_b$. As solute builds up at the surface of the membrane, the gelation concentration ($C_w=C_b$) is eventually reached, which limits flux through the membrane. From the above equation, the gel layer thickness (l) is provided by:

$$l = \left(\frac{D}{J_v}\right) \ln\left(\frac{C_w}{C_b}\right) \quad (2)$$

The graph 700 was generated using equation 2, and assuming that D for albumin in water is $7.1 \times 10^{-11}$ m²/s, $J=1.6 \times 10^{-4}$ m/s, and $C_b$ is about 60 g/l. The values were based on the literature for a membrane with a 100 kDa pore size. As illustrated, using the provided conditions, the gel layer thickness approaches an asymptote at about 2 μm. Accordingly, under normal conditions the gel layer thickness that would eventually form absent a protein gel disruption layer can be estimated to be between about 1 μm and about 2 μm. Similar calculations could be made to estimate the height of the protein gel layer for membranes with different pore sizes.

Figure 8:
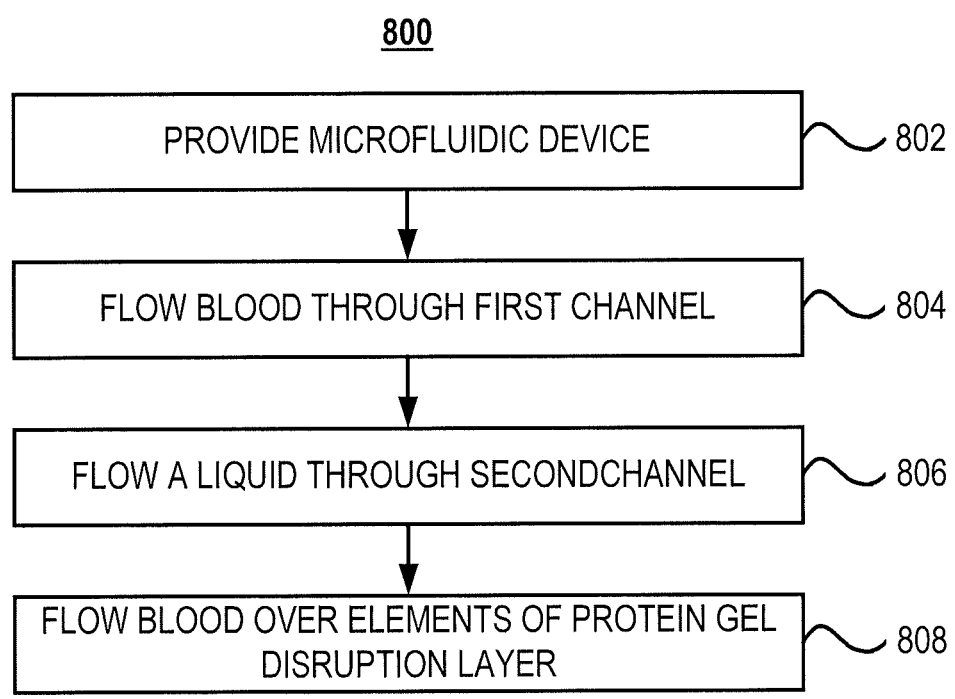
FIG. 8 illustrates a flow chart of an example method for conducting dialysis using the system illustrated in FIG. 1A.

FIG. 8 illustrates a flow chart of an example method 800 for conducting dialysis. The method 800 includes providing a microfluidic device (step 802). Blood is flowed through a first channel of the microfluidic device (step 804) and a treatment fluid is flowed through a second channel of the microfluidic device (step 806). The blood is flowed over the elements of a protein gel disruption layer (step 808). As the blood is flowed through the first channel of the microfluidic and over the elements of the protein gel disruption layer, waste is removed from the blood while avoiding the formation of a protein gel layer.

As set forth above, and referring to FIG. 2, a microfluidic flow device is provided (step 802). The microfluidic flow device can be any of the microfluidic flow devices described herein. In general, the microfluidic flow device includes a first flow channel 204 defined in a first polymer layer 202 and a second flow channel 208 defined in a second polymer layer 206. The first flow channel 204 and the second flow channel 208 overlap and run substantially parallel to one another. At the overlapping portions, the first flow channel 204 and the second flow channel 208 are separated by a membrane 210 that enables fluidic communication between the first flow channel 204 and the second flow channel 208. A protein gel disruption layer 212 is disposed in the blood flow channel (e.g., first flow channel 204). The protein gel disruption layer 212 includes a plurality of elements that extend across the first flow channel 204. In some implementations, the height of the protein gel disruption layer 212 is configured to be about the height of the gel protein layer or boundary layer that would form near the membrane 210 if the microfluidic device did not include a protein gel disruption layer 212. For example, the elements of the protein gel disruption layer 212 may have a height of at least about 1 μm and terminate a distance from the center of the thickness of the membrane that is less than or equal to about ⅓ of the height of the first flow channel 204. In some implementations, the first flow channel is configured differently than the second flow channel. For example, the first flow channel may include rounded edges, an anticoagulant coating, or may otherwise have its shape optimized for carrying shear sensitive fluids, such as blood. These optimization can reduce the chances of clots forming in the first flow channel.

Next, blood is flowed through blood flow channels of the provided microfluidic device (step 804). As illustrated in FIG. 1A, in some implementations, the blood is flowed into the microfluidic device from a blood reservoir 104 by a pump 106. In other implementations, the blood is flowed into the microfluidic device directly from a patient. In some implementations, the microfluidic device includes a manifold that distributes the blood to each of the blood flow channels within the microfluidic device. In some implementations, a blood thinner or anticoagulant, such as warfarin or heparin, is added to the blood to prevent the blood from clotting within the microfluidic device or another component of the system 100.

A treatment fluid, such as dialysate, is then flowed through the second flow channel of the provided microfluidic device (step 806). In some implementations, such as the tri-layer configuration illustrated in FIG. 6, an infusate is also flowed through an infusate flow channel of the provided microfluidic device. In some implementations, the blood flows in one direction through the microfluidic device and the treatment fluid flows in the opposite direction through the microfluidic device.

As blood flows through the first flow channel, the blood flows over the elements of a protein gel disruption layer (step 808). As described above, the protein gel disruption layer can include a screen, a mesh, a plurality of topographical features embedded in or affixed to the membrane, joists, struts, or a combination thereof. As the blood flows over the elements of the protein gel disruption layer, the elements of the protein gel disruption layer create minor disturbances in the laminar flow of the blood through the first flow channel. In some implementations, the disturbances in the laminar flow are substantially close to the membrane—for example, between about 1 µm and 5 µm from the surface of the membrane. In some implementations, the disturbances in the laminar flow of the blood reduce the formation of a protein gel layer along the surface of the membrane. For example, the disturbances can dislodge or move proteins that accumulate near the membrane back into the bulk of the blood flowing through the first flow channel.

As the blood flows through the first flow channel, waste is removed from the blood (step 810). As blood flows through the blood flow channel, urea, potassium, phosphorus, and other waste materials within the blood diffuse across the membrane and into the dialysate flowing through the second flow channel. In some implementations, infusate can pass into the blood from an infusate channel. Because the protein gel disruption layer reduces the boundary layer or gel layer typically formed at the blood-membrane interface, the microfluidic device can maintain its efficiency over the course of a hemodialysis or hemofiltration session.

Figure 9:
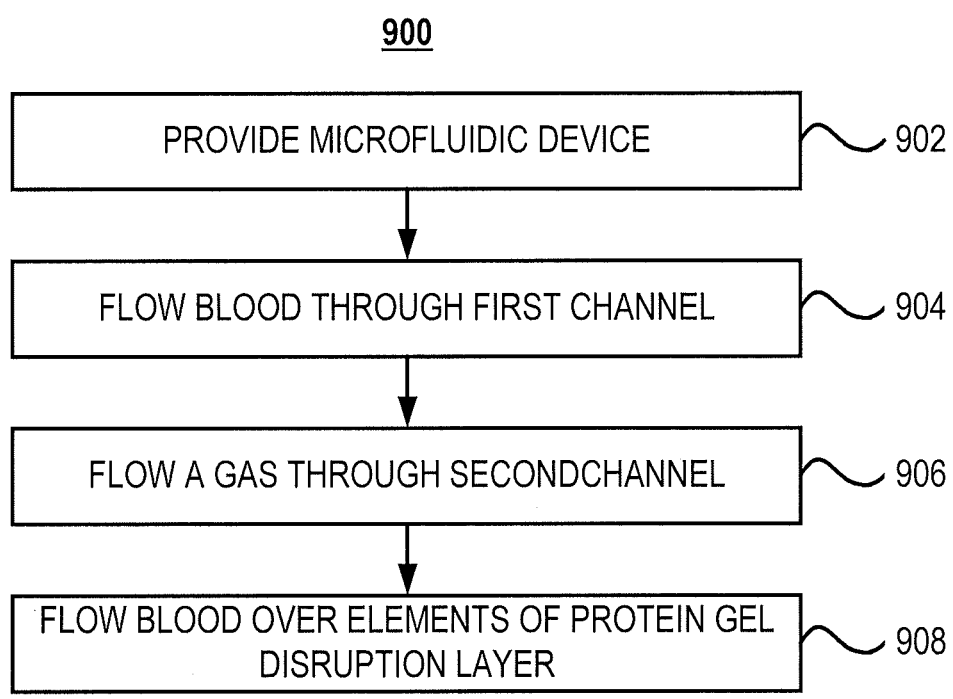
FIG. 9 illustrates a flow chart of an example method for oxygenating partially deoxygenated blood using the system illustrated in FIG. 1A.

FIG. 9 illustrates a flow chart of an example method 900 for oxygenating partially deoxygenated blood. The method 900 includes providing a microfluidic device (step 902). Blood is flowed through a first channel of the microfluidic device (step 904) and oxygen is flowed through a second channel of the microfluidic device (step 906). The blood is flowed over the elements of a protein gel disruption layer (step 908). As the blood is flowed through the first channel of the microfluidic and over the elements of the protein gel disruption layer, oxygen diffuses into the blood while avoiding the formation of a protein gel layer.

As set forth above, and referring to FIG. 2, a microfluidic flow device is provided (step 902). The microfluidic flow device can be any of the microfluidic flow devices described herein. In general, the microfluidic flow device includes a first flow channel 204 defined in a first polymer layer 202 and a second flow channel 208 defined in a second polymer layer 206. The first flow channel 204 and the second flow channel 208 overlap and run substantially parallel to one another. At the overlapping portions, the first flow channel 204 and the second flow channel 208 are separated by a membrane 210 that enables fluidic communication between the first flow channel 204 and the second flow channel 208. A protein gel disruption layer 212 is disposed in the blood flow channel (e.g., first flow channel 204). The protein gel disruption layer 212 includes a plurality of elements that extend across the first flow channel 204. In some implementations, the height of the protein gel disruption layer 212 is configured to be about the height of the gel protein layer or boundary layer that would form near the membrane 210 if the microfluidic device did not include a protein gel disruption layer 212. For example, the elements of the protein gel disruption layer 212 may have a height of at least about 1 µm and terminate a distance from the center of the thickness of the membrane that is less than or equal to about ⅓ of the height of the first flow channel 204. In some implementations, the first flow channel is configured differently than the second flow channel. For example, the first flow channel may include rounded edges, an anticoagulant coating, or may otherwise have its shape optimized for carrying shear sensitive fluids like blood. These optimizations can reduce the chances of clots forming in the first flow channel.

Next, blood is flowed through blood flow channels of the provided microfluidic device (step 904). As illustrated in FIG. 1A, in some implementations, the blood is flowed into the microfluidic device from a blood reservoir 104 by a pump 106. In other implementations, the blood is flowed into the microfluidic device directly from a patient. In some implementations, the microfluidic device includes a manifold that distributes the blood to each of the blood flow channels within the microfluidic device. In some implementations, a blood thinner or anticoagulant, such as warfarin or heparin, is added to the blood to prevent the blood from clotting within the microfluidic device or another component of the system 100.

Oxygen or a mixture of gases is then flowed through the second flow channel of the provided microfluidic device (step 906). As the blood and oxygen pass through the microfluidic device, oxygen passes into the blood. In some implementations, the blood flows in one direction through the microfluidic device gases flow in the opposite direction through the microfluidic device.

As blood flows through the first flow channel, the blood flows over the elements of a protein gel disruption layer (step 908). As described above, the protein gel disruption layer can include a screen, a mesh, a plurality of topographical features embedded in or affixed to the membrane, joists, struts, or a combination thereof. As the blood flows over the elements of the protein gel disruption layer, the elements of the protein gel disruption layer create minor disturbances in the laminar flow of the blood through the first flow channel. In some implementations, the disturbances in the laminar flow are substantially close to the membrane—for example, between about 1 µm and 5 µm from the surface of the membrane. In some implementations, the disturbances in the laminar flow of the blood reduce the formation of a protein gel layer along the surface of the membrane. For example, the disturbances can dislodge or move proteins that accumulate near the membrane back into the bulk of the blood flowing through the first flow channel.

As the blood flows through the first flow channel, oxygen from the gas channel diffuses across the membrane and into the blood of the first flow channel to oxygenate the partially deoxygenated blood. Because the protein gel disruption layer reduces the boundary layer or gel layer typically formed at the blood-membrane interface, the microfluidic device can maintain its efficiency over the course blood oxygenation treatment.

The invention may be embodied in other specific forms without departing from the spirit or essential characteristics thereof. The forgoing implementations are therefore to be considered in all respects illustrative, rather than limiting of the invention.

What is claimed:

1. A microfluidic blood filtration device comprising:
 a first layer defining a first channel configured for liquid flow therein;
 a second layer defining a second channel configured for liquid flow therein, the second channel overlapping the first channel along a substantial portion of the length of the first channel;
 a membrane separating the first channel from the second channel, the membrane being configured to allow passage of liquid through the membrane; and
 a protein gel disruption layer adjacent to or positioned within the first channel, the protein gel disruption layer including a plurality of elements extending at least partially across the first channel, the elements having a height of at least about 1 μm and having an end terminating at a distance from the center of the thickness of the membrane that is less than or equal to about ⅓ of a height of the first channel.

2. The microfluidic blood filtration device of claim 1, further comprising:
 a third layer defining a third channel therein, the third channel overlapping the first channel; and
 a second membrane separating the third channel from the first channel.

3. The microfluidic blood filtration device of claim 1, wherein the plurality of elements extend fully across the first channel.

4. The microfluidic blood filtration device of claim 1, wherein the height of the first channel is between about 50 μm and about 100 μm.

5. The microfluidic blood filtration device of claim 1, wherein the elements of the gel disruption layer that extend across the first channel comprise a plurality of topographical features integrated into the membrane.

6. The microfluidic blood filtration device of claim 1, wherein the gel disruption layer comprises a screen disposed in the first channel and adjacent to the membrane.

7. The microfluidic blood filtration device of claim 6, wherein the screen defines a plurality of screen openings, wherein a dimension of each of the plurality of screen openings along the length of the channel is between about 100 μm and about 5 mm.

8. The microfluidic blood filtration device of claim 6, wherein the screen comprises one of a biocompatible metal, polyester, and a polyamide.

9. The microfluidic blood filtration device of claim 1, wherein a pitch between each of the plurality of elements is between about 100 μm and about 5 mm.

10. The microfluidic blood filtration device of claim 1, wherein the length of the first channel is between about 5 cm and about 30 cm.

11. The microfluidic blood filtration device of claim 1, wherein a height of each of the plurality of elements is between about 1 μm and about 3 μm.

12. The microfluidic blood filtration device of claim 1, wherein the first channel is configured for blood flow and the second channel is configured for infusate, or dialysate flow.

13. The microfluidic blood filtration device of claim 1, wherein each of the plurality of elements extends from a surface of the first channel opposite the membrane toward the membrane.

14. The microfluidic blood filtration device of claim 1, wherein each of the plurality of elements are integral to the first layer and extend across the first channel adjacent to the membrane.

15. A microfluidic blood filtration device comprising:
 a first layer defining a first channel configured for liquid therein;
 a second layer defining a second channel configured for liquid therein, the second channel overlapping the first channel along a substantial portion of the length of the first channel;
 a membrane separating the first channel from the second channel, the membrane being configured to allow passage of liquid through the membrane; and
 a protein gel disruption layer adjacent to or positioned within the first channel, the protein gel disruption layer including a plurality of elements extending at least partially across the first channel, the elements having a height of at least about 1 μm and having an end terminating at a distance from the center of the thickness of the membrane that is less than or equal to about ⅓ of a height of the first channel,
 wherein the plurality of elements of the protein gel disruption layer defines a number of openings in the protein gel disruption layer that allow fluid communication between the membrane and the first channel.

* * * * *